(12) United States Patent
Wulf

(10) Patent No.: US 6,632,401 B1
(45) Date of Patent: Oct. 14, 2003

(54) DEVICE FOR THE DETECTION OF A FLUORESCENT DYE

(75) Inventor: Jurgen Wulf, Ueberlingen (DE)

(73) Assignee: Bodenseewerk Perkin-Elmer GmbH (DE)

(*) Notice: Subject to any disclaimer, the term of this patent is extended or adjusted under 35 U.S.C. 154(b) by 0 days.

(21) Appl. No.: 09/286,849

(22) Filed: Apr. 6, 1999

(30) Foreign Application Priority Data

Apr. 14, 1998 (DE) .......................................... 198 16 487

(51) Int. Cl.[7] .............................................. G01N 21/64
(52) U.S. Cl. ................................. 422/82.08; 250/458.1
(58) Field of Search .......................... 422/82.07, 82.08; 250/458.1, 459.1; 436/172

(56) References Cited

U.S. PATENT DOCUMENTS

| | | | |
|---|---|---|---|
| 4,583,860 A | 4/1986 | Butner | 356/446 |
| 4,685,059 A * | 8/1987 | Yamamoto | 364/415 |
| 4,770,517 A | 9/1988 | Sakuma | |
| 4,867,559 A * | 9/1989 | Bach | 356/73 |
| 4,965,454 A * | 10/1990 | Yamauchi et al. | 250/372 |
| 5,118,181 A | 6/1992 | Yifrach et al. | 356/30 |
| 5,164,844 A | 11/1992 | Granger | 358/474 |
| 5,408,312 A | 4/1995 | Pries et al. | 356/236 |
| 5,533,509 A * | 7/1996 | Koashi et al. | 128/633 |
| 5,555,123 A | 9/1996 | Kaplan | 359/197 |
| 5,585,639 A | 12/1996 | Dorsel et al. | 250/458.1 |
| 5,598,008 A | 1/1997 | Livoni | 250/586 |
| 5,636,015 A | 6/1997 | Imura et al. | 356/72 |
| 5,751,839 A | 5/1998 | Drocurt et al. | 382/133 |
| 5,796,112 A | 8/1998 | Ichie | 250/458.1 |
| 5,838,429 A * | 11/1998 | Hahn | 356/39 |

FOREIGN PATENT DOCUMENTS

| | | |
|---|---|---|
| DE | 43 07 042 A1 | 9/1994 |
| EP | 0 360 233 A2 | 3/1990 |
| EP | 801297 | 10/1997 |
| JP | 33-4395 | 3/1958 |
| JP | 54-118298 | 9/1979 |
| JP | 57-120845 | 7/1982 |
| JP | 8-015156 | 1/1996 |
| JP | 8-313349 | 11/1996 |
| JP | 9049794 | 2/1997 |
| JP | 10-142152 | 5/1998 |
| WO | WO 97/04302 | 2/1997 |

OTHER PUBLICATIONS

"Scanning Laser Microscopy Lab, Our Microscopes," University of Waterloo, http://www.science.uwaterloo.ca/physics/research/confocal/microsc.html, last updated Aug. 10, 1999, five pages.

"Abakus 3.5mm f/8 High Definition Stadium Lens," Innovision Optics, Inc., Santa Monica, CA, date unknown, one page.

"Applications of Fixed Focus Technology in Laser Marking Systems, Fixed Field Size vs. VariField™," Alase Technologies, Pepperell, MA, http://www.alase.com/applications/ftheta.html, 1997–2002, two pages.

* cited by examiner

*Primary Examiner*—Jeffrey Snay
(74) *Attorney, Agent, or Firm*—Harness, Dickey & Pierce, P.L.C.

(57) ABSTRACT

The present invention relates to a device for the detection of a fluorescent dye in a sample, comprising a radiation source with the aid of which light for exciting the fluorescent dye to be detected can be transmitted into the sample applied to a carrier, and a detecting device for detecting fluorescent light which has been emitted by the fluorescent dye to be detected. The present invention is characterized by a hollow space having an internal high-reflectance surface, a first aperture directed towards the sample, and a second aperture located opposite the detecting device.

24 Claims, 2 Drawing Sheets

DEVICE FOR THE DETECTION OF A FLUORESCENT DYE

FIELD OF THE INVENTION

The present invention relates to a device for the detection of a fluorescent dye in a sample, comprising a radiation source means with the aid of which light for exciting the fluorescent dye to be detected can be transmitted into the sample applied to a carrier, and a detecting means for detecting fluorescent light which has been emitted by the fluorescent dye to be detected.

BACKGROUND ART

Such devices in which fluorescent light is detected by a photomultiplier means are used e.g. for analyses in the field of molecular biology and genetic engineering. For this purpose, a sample is applied to a carrier and temporarily brought into contact with a fluorescent marker. Those substances to be analyzed which have an affinity for the marker agglutinate the marker and, consequently, they can be excited to emit fluorescent light. It follows that, due to the excitability of fluorescence, the marker-agglutinating property of the substance to be analyzed becomes visible, whereby conclusions can be drawn with regard to the nature of the sample material.

However, a disadvantage of the devices known from the prior art is to be seen in the fact that the fluorescent light, which has no preferred direction and which is therefore emitted into the whole solid angle, can only be detected from a small solid angle area with the aid of a photomultiplier means. It follows that the detection sensitivity of the known devices is only very small.

SUMMARY OF THE INVENTION

In view of this disadvantage of the devices according to the prior art, it is the object of the present invention to improve the known device for the detection of a fluorescent dye in such a way that its detection sensitivity is increased.

This object is achieved by a device of the type cited at the start, which is characterized by a hollow space having an internal high-reflectance surface, a first aperture directed towards the sample, and a second aperture located opposite the detecting means.

Due to the fact that the means for exciting the fluorescent dye to be detected, the surface of which has the sample applied thereto, is located opposite the first aperture of the hollow space, the fluorescent light is emitted from a large solid angle into the hollow space. Since the hollow space is additionally provided with an internal high-reflectance surface, the light transmitted into the hollow space can propagate in said hollow space until it is detected by a detector.

It follows that, in comparison with the prior art, the fluorescent light can be detected from a much larger solid angle, whereby the detection sensitivity of the device is greatly increased in comparison with the known devices.

According to a preferred embodiment of the present invention, the high-reflectance surface consists of barium sulfate or spectralon. Such surfaces have a reflectance of up to 99.8%. Hence, the reflectance losses in the hollow space can be kept very small.

According to a preferred embodiment, the radiation source means can be provided in such a way that it emits monochromatic light, especially laser light. The advantage of monochromatic light is to be seen in the fact that the influence of monochromatic light on the fluorescent light emitted can be controlled much better, e.g. by purposeful absorption. The advantage of laser light is the comparatively high spot intensity which can be achieved by means of the laser light. Correspondingly high excitation rates of the fluorescent dye to be detected are therefore obtained.

Furthermore, a beam forming means, especially a beam expansion means, can be provided after the radiation source means. This measure permits an adaptation of the light beam emitted by the radiation source means to the dimensions of the desired laser spot size.

According to a preferred embodiment, the radiation source means and the carrier can have provided between them a scanning means with the aid of which rays emitted by the radiation source can be guided over the carrier. A plurality of samples applied to the carrier in the form of an array can, in this way, sequentially be excited to exhibit fluorescence and the resultant fluorescent light can be detected without any necessity of carrying out a time-consuming exchange of samples, including the cleaning of the carrier and the like, or a mechanical displacement of the sample relative to the carrier.

According to another advantageous embodiment, a focussing lens system is provided for focussing the excitation light onto the sample. The spot intensity of the excitation light can be increased still further in this way, whereby the resolution and intensity of the secondary light is increased.

According to an advantageous embodiment, the focussing lens system is an F/θ lens in the case of which an image of the scanning ray bundle is formed according to the so-called F/θ condition y'=Fxθ, wherein y' is the imaging coordinate, F the focal length and θ the angle included by the scanning ray bundle and the optical axis. This permits a focussing of beams of light independently of the distance to the optical axis, and the focussing effect can therefore be intensified in comparison with conventional lenses. A change of the angle of the deflection mirror is therefore converted into a proportional deviation y'.

According to another advantageous further development of all the above-mentioned embodiments, a beam divider can be provided in such a way that, by means of said beam divider, part of the light emitted by the radiation source means can be directed onto the sample and part of the fluorescent light emitted by the fluorescent dye to be detected can be conducted into the hollow space. By means of this measure, a compact and easily operable setup of the device according to the present invention can be realized.

In this connection, the beam divider can be provided in the form of a dichroic beam divider which, on the one hand, reflects the excitation light with high efficiency and deflects therefore most of the excitation light towards the sample and, on the other hand, permits passage of the fluorescent light with high efficiency, the fluorescent light being thus conducted into the hollow space.

According to a further preferred embodiment of the present invention, further detecting means can be provided in complementary apertures located opposite each of said further detecting means in the hollow space.

These further means can be provided for detecting fluorescent light resulting from different excitation levels of the fluorescent dye to be detected and having different wavelengths consequently.

It follows that this setup permits measurement of a dye at one excitation wavelength, but simultaneously at different wavelengths of the fluorescent light. Since such simultaneous measurements of the fluorescent light at different wavelengths can only be carried out with very great effort by means of the known devices, the present invention permits the time required for carrying out the measurement of the fluorescent light at different wavelengths to be reduced by a factor N in a simple manner, when N stands for the number of different wavelengths of the fluorescent light.

In addition, the further detecting means according to this preferred embodiment can be used for detecting further fluorescent dyes at the same time. It is therefore possible to measure the fluorescent light of different fluorescent dyes with different excitation wavelengths at the same time. Just as in the setup for measuring the fluorescent light at different wavelengths of a fluorescent dye, a reduction of the measurement time by a factor N is obtained also in cases in which several fluorescent dyes are measured, when N stands for the number of fluorescent dyes to be detected at the same time.

According to a further preferred embodiment, a combination of the two above-mentioned measurements is possible. Hence, the fluorescent light of a plurality of fluorescent dyes can be detected in the case of respective different wavelengths.

According to a preferred embodiment, the detecting means are arranged in their respective apertures in the hollow space in a light-tight arrangement. This eliminates a further source of losses for the fluorescent light and stray light.

According to a preferred embodiment, each detecting means can be provided with a photomultiplier means. In addition, each detecting means can be provided with a color filter means which is adapted to the wavelength of the fluorescent light to be detected by said color filter means. If necessary, each detecting means can be provided with a collimator lens.

According to a further preferred embodiment, a blocking filter device can be provided in front of the first aperture of the hollow space, said blocking filter device blocking the light used for excitation and transmitting the fluorescent light to be detected. By means of this measure the laser light used for excitation can be prevented from being scattered into the hollow space where it would have a disadvantageous influence on the detection of the fluorescent light. Such blocking filter devices can be provided in a particularly simple manner, e.g. in the form of absorbing filters (Anlauffiltern) and/or interference filters, especially when monochromatic light is used.

In accordance with an advantageous embodiment, such a blocking filter device can be realized by an interference filter and/or an absorbing filter known in the prior art.

BRIEF DESCRIPTION OF THE DRAWINGS

Further advantages and features of the present invention can be seen from the following exemplary description of preferred embodiments of the present invention, which makes reference to the drawings in which.

DETAILED DESCRIPTION OF THE PREFERRED EMBODIMENTS

Figure 1:
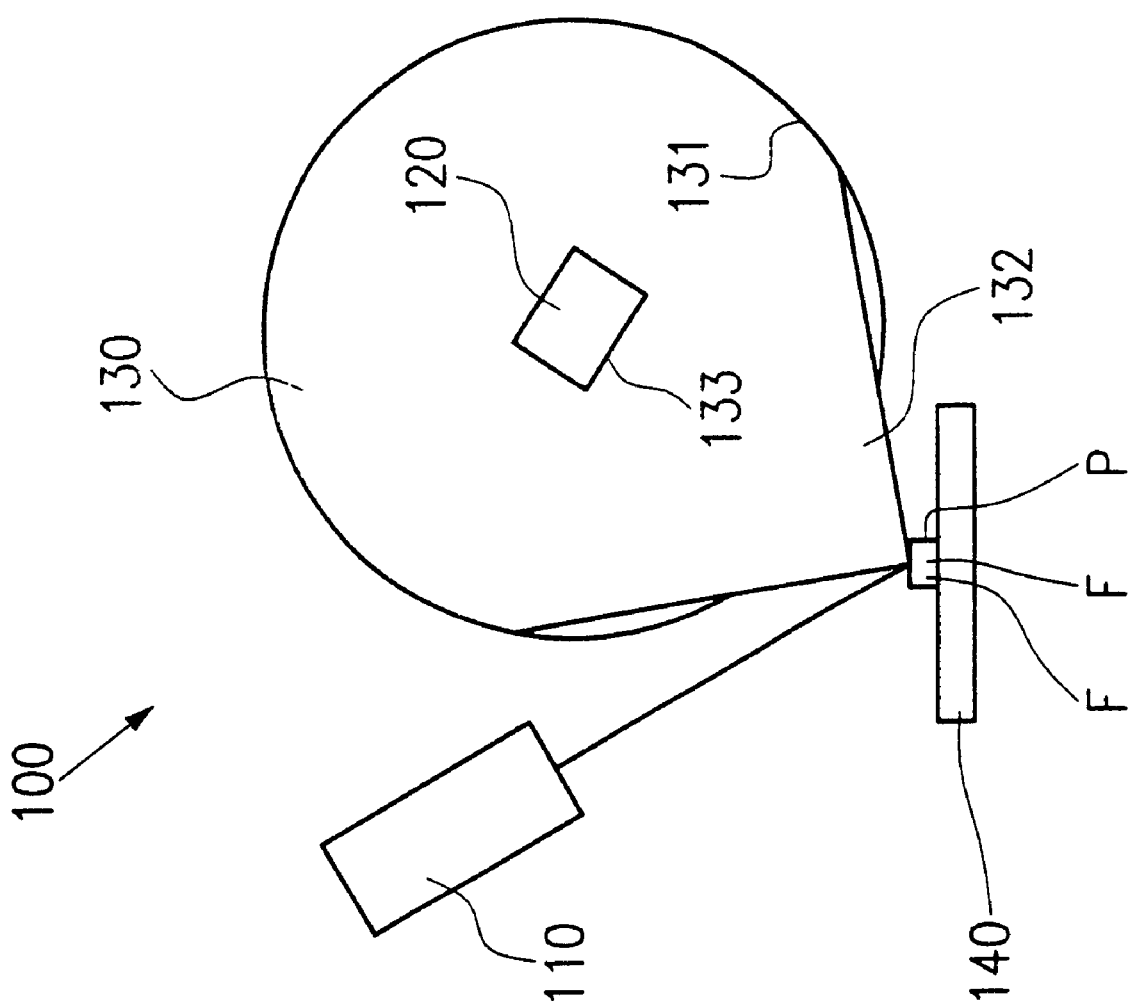
FIG. 1 shows a schematic representation of a first embodiment of the present invention.

FIG. 1 shows a first embodiment of a device 100 for detecting a fluorescent dye F in a sample P according to the present invention.

The device 100 comprises a radiation source means 110, a carrier 140 having applied thereto the sample P containing the fluorescent dye F to be detected, and a hollow space 130 having a spherical shape in the present embodiment. This hollow space 130 is provided with a first aperture 132 located opposite the carrier 140 with the sample P.

The hollow space 130 comprises an internal high-reflectance surface 131 consisting e.g. of barium sulfate or spectralon.

By means of this special coating an internal surface reflectance of 99.8% can be achieved.

In addition, a second aperture 133 is provided in said hollow space 130, in which a detector 120 for detecting fluorescent light emitted by the fluorescent dye F to be detected is inserted, e.g. a photomultiplier device.

In the following, a brief description of the mode of operation of device 100 will be given.

The light containing the excitation wavelength or monochromatic light of the excitation wavelength, e.g. laser light, is transmitted into the sample P by the radiation source means 110.

This light is used for exciting the fluorescent dye F.

The fluorescent light emitted by the fluorescent dye is transmitted into the hollow space 130 and finally detected by the detector 120 at the high-reflectance surface 131 after several diffuse reflections.

Since the sample is located opposite the aperture of the hollow space 132 and since, moreover, the fluorescent light generally has no preferred direction, the percentage of fluorescent light transmitted into the hollow space 130, where it can finally be detected, is, in comparison with the prior art, substantially higher in the present setup.

It follows that, in comparison with devices known from the prior art in which lens systems or light guides and the respective detectors are used, the solid angle from which fluorescent light is collected can be increased significantly in the device 100, whereby an increased detection sensitivity can be achieved.

The device 100 shown in FIG. 1 can be modified in many ways.

The hollow space 130 can, for example, also exhibit other geometrical shapes, e.g. a cubic shape or the like. However, in comparison with the spherical design shown in FIG. 1, the number of reflections of the fluorescent light in the hollow space may increase until the time of detection by the detector, and this may possibly lead to an increase in the reflectance losses in the hollow space. Non-uniform illumination may be caused as well.

The detector 120 is provided in the form of a photomultiplier in the present embodiment. A color filter means can preferably be arranged in front of sad photomultiplier, said color filter means being adapted to the wavelength emitted by the fluorescent dye F to be detected.

If the reflectance losses in the hollow space 130 are to be reduced still further, it is advisable to insert the detector 120 into the aperture 133 in a light-tight arrangement.

Furthermore, if necessary, the detector may be provided with a collimator lens.

While in the case of the embodiment described in connection with FIG. 1 only a monochromatic light beam is transmitted into the sample P, the device shown in FIG. 1 can also be operated with two or more excitation wavelengths. For this purpose, additional radiation source means can be provided, the excitation can be modulated in the frequency range, and the fluorescent light at the respective frequency can be detectted by means of a detector which is controlled accordingly.

In order to use the described device for the detection of fluorescent light of a specific fluorescent dye, it will suffice to adjust the excitation light source and, if provided, the colour filter in front of the photomultiplier to the fluorescent dye.

For detecting fluorescein, which can be excited to exhibit fluorescence at 488 nm, it is necessary to expose the sample to light of this wavelength, e.g., by means of an argon laser. Since the fluorescent light is emitted at 520 nm, the color filter used would have to be transmitting in this range. This applies analogously to CY5 which can be excited at 633 nm and which emits fluorescent light at 670 nm.

Figure 2:
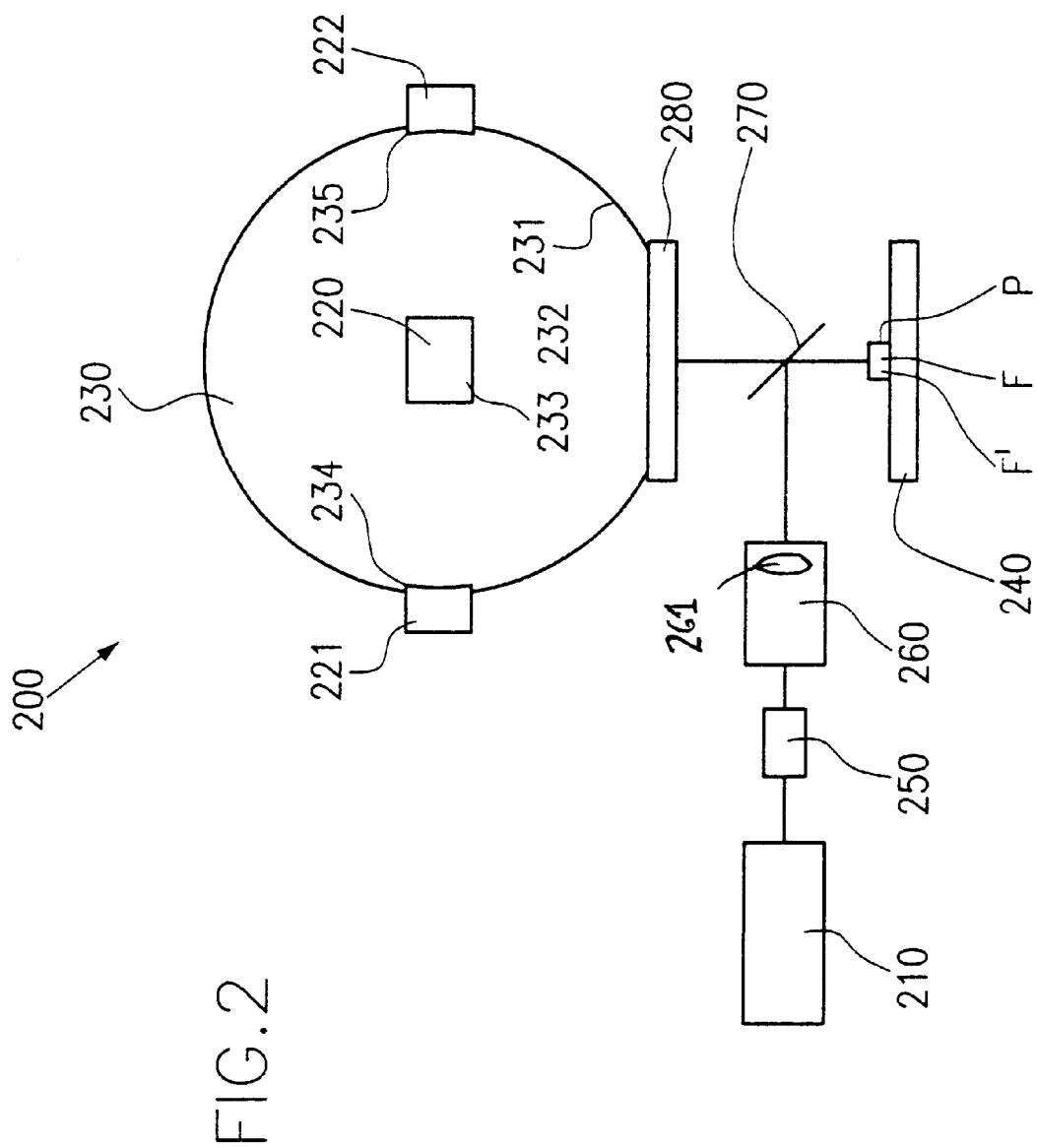
FIG. 2 shows a schematic representation of a second embodiment of the present invention.

FIG. 2 shows a second embodiment of a device 200 for detecting a fluorescent dye F in a sample P.

This device differs from the device shown in FIG. 1 in that, in addition to a first detecting means 220, further detecting means 221 and 222, a beam expansion means 250, a scanning means 260, a beam divider 270 and a blocking filter 280 are provided.

In order to avoid repetitions, only these different features will be explained in the following and with regard to the remaining components reference will simply be made to the description in connection with FIG. 1. In this context, it should be pointed out that the reference numerals of the respective corresponding components only differ with regard to the first figure.

In the second embodiment, two detectors 221 and 222 are provided, which are inserted into respective apertures 234 and 235 in the hollow space 230.

The detectors 221 and 222 can have the same structural design as detector 220 or they can specially be adapted to a fluorescent light whose wavelength differs from that of the fluorescent light to be detected by detector 220.

Although only three detectors 220, 221 and 222 are shown in the embodiment according to FIG. 2, it is apparent that additional detectors may be provided.

On the one hand, this setup permits a detection of fluorescent light of the same fluorescent dye F, said fluorescent light resulting from different excitation states.

Alternatively, the detectors may also be implemented in such a way that they are provided for detecting at least one further fluorescent dye F' at the same time, as can be seen in FIG. 2. For this purpose, it may be necessary to transmit light at different excitation wavelengths into the sample P.

It goes without saying that also arbitrary combinations of the two above-described operating methods are possible; i.e. this kind of arrangement may be used for detecting the fluorescent light of a plurality of fluorescent dyes F and F' at their different wavelengths.

Furthermore, the device 200 includes a beam forming means in the form of a beam expansion means 250. With the aid of this means, the beam emitted by the radiation source means can be expanded, whereby focussing in connection with the focussing lens system, which will be described hereinbelow, can be improved.

In addition to the beam expansion means 250 shown, also other beam forming means, e.g. a pinhole and the like, can be used if this should be necessary in view of the sample geometry.

The beam expansion means 250 is followed by the scanning means 260. With the aid of this scanning means 260, a beam emitted by the radiation source means 210 can be guided over the carrier in two dimensions. With the aid of this setup, a plurality of samples applied to the carrier in the form of an array can sequentially be excited to exhibit fluorescence without any necessity of carrying out a time-consuming exchange of samples, including the cleaning of the carrier 240 and the like.

The scanning means 260 further comprises a focussing lens system 261 for focussing the excitation light onto the sample. The spot intensity of the excitation light can be increased still further in this way, and, consequently, the spatial resolution and the irradiance of the fluorescent light can be increased as well.

It will be adavantageous to use as a focussing lens system an F/θ lens in the case of which an image of the scanning beam is formed according to the so-called F/θ condition y'=Fxθ, wherein y' is the image coordinate, F the focal length and θ the angle included by the scanning ray bundle and the optical axis.

This permits a focussing of beams of light independently of the distance to the optical axis. Hence, the focussing effect can be intensified in comparison with a conventional lens. In addition, a more uniform focussing over the area within which the sample is provided can be achieved by means of such an F/θ lens.

Furthermore, the second embodiment comprises a beam divider 270. The beam divider is provided between the carrier 240 for the sample and the aperture 232 of the hollow space. On the one hand, the beam divider 270 directs part of the light emitted by the radiation source means 210 onto the sample P. On the other hand, the beam divider permits passage of part of the fluorescent light emitted by the fluorescent dye F to be detected so that this light can enter the hollow space 230 where it can be detected by the detector 230 and the detectors 231 and 222, respectively.

In accordance with an advantageous embodiment, the beam divider 270 can comprise a dichroic beam divider. This special beam divider is implemented in such a way that, on the one hand, it reflects the excitation light with high efficiency and deflects therefore most of the excitation light towards the sample and that, on the other hand, it permits passage of the fluorescent light with high efficiency.

Furthermore, a blocking filter device 280 is provided in front of the aperture 232 of the hollow space 230 in the second embodiment. This blocking filter device 280 is opaque to the light, which is used for excitation and which is scattered in the direction of the hollow space 230, and transmits the fluorescent light to be detected. Such blocking filter devices can be realized e.g. by an interference filter, an absorbing filter, or a combination of such filters.

In addition, said blocking filter device 280 can also be used for blocking even the amount of laser light which is conducted towards the hollow space in spite of the beam divider 270 so that only the light which has been emitted by the fluorescent dye F is transmitted into the hollow space.

Although, in the second embodiment, the additional detectors 221 and 222, the beam expansion means 250, the scanning means 260, the beam divider 270 and the blocking filter device 280 have been shown in common in one embodiment, it should be pointed out that these features are independent of one another and that, consequently, each individual one of these features can be used, if necessary, so as to achieve the advantages described in connection with the respective feature.

What is claimed is:

1. A device for the detection of a fluorescent dye in a sample, said device comprising
   a radiation source configured to transmit light to excite the fluorescent dye to be detected into the sample applied to a carrier,
   a detector configured to detect fluorescent light from the fluorescent dye to be detected,
   a hollow space having an internal high-reflectance surface, a first aperture directed towards the sample, and a second aperture located opposite the detector, and
   a dichroic beam divider configured to direct part of the light emitted by the radiation source onto the sample and to conduct part of the fluorescent light emitted by the fluorescent dye to be detected into the hollow space.

2. A device according to claim 1, wherein the hollow space has a substantially spherical shape.

3. A device according to claim 1, wherein the high-reflectance surface comprises barium sulfate or spectralon.

4. A device according to claim 1, wherein the radiation source emits monochromatic light.

5. A device according to claim 4, wherein the monochromatic light is laser light.

6. A device according to claim 1, wherein a beam expander is provided after the radiation source.

7. A device according to claim 1, wherein the radiation source and the carrier have provided between them a scanner configured to guide rays emitted by the radiation source over the carrier.

8. A device according to claim 7, wherein said scanner comprises a focusing lens configured to focus rays emitted by the radiation source onto the sample.

9. A device according to claim 8, wherein said focusing lens comprises an F/θ lens.

10. A device according to claim 1, wherein said detector is a first detector, and further comprising at least a second detector and a complementary aperture located opposite one another in the hollow space.

11. A device according to claim 10, wherein said second detector is configured to detect a wavelength different from that of the first detector.

12. A device according to claim 1, wherein the detector comprises a photomultiplier.

13. A device according to claim 12 comprising a plurality of detectors, each having a color filter adapted to the wavelength of the fluorescent light to be detected by a corresponding said detector.

14. A device according to claim 1, wherein the detector is provided with a collimator lens.

15. A device according to claim 1, further comprising a blocking filter in front of the first aperture of the hollow space, said blocking filter opaque to the excitation light and transmissive to the fluorescent light to be detected.

16. A device according to claim 15, wherein the blocking filter is provided with an interference filter, an absorbing filter, or both an interference filter and an absorbing filter.

17. A device according to claim 1, wherein the detector is arranged in the second aperture in a light-tight arrangement.

18. A device for the detection of a fluorescent dye in a sample, said device comprising
   a radiation source configured to transmit light to excite the fluorescent dye to be detected into the sample applied to a carrier,
   a detector configured to detect fluorescent light from the fluorescent dye to be detected,
   a hollow space having an internal; high-reflectance surface, a first aperture directed towards the sample, and a second aperture located opposite the detector, and
   a blocking filter in front of the first aperture of the hollow space, the blocking filter opaque to the excitation light and transmissive to the fluorescent light to be detected.

19. A device according to claim 18, wherein the blocking filter is provided with an interference filter, an absorbing filter, or both an interference filter and an absorbing filter.

20. A device according to claim 18, wherein the radiation source and the carrier have provided between them a scanner configured to guide rays emitted by the radiation source over the carrier.

21. A device according to claim 20 wherein said scanner comprises a focusing lens configured to focus the rays emitted by the radiation source onto the sample.

22. A device according to claim 21 wherein said focusing lens system comprises an F/θ lens.

23. A device according to claim 18 wherein the detector is arranged in the second aperture in a light-tight arrangement.

24. A device for the detection of a fluorescent dye in a sample, said device comprising
   a radiation source configured to transmit light to excite the fluorescent dye to be detected into the sample applied to a carrier,
   a detector configured to detect fluorescent light from the fluorescent dye to be detected, and
   a hollow space having an internal high-reflectance surface, a first aperture directed towards the sample, and a second aperture located opposite the detector,
   wherein the radiation source and the carrier have provided between them a scanner configured to guide rays emitted by the radiation source over the carrier, and further
   wherein said scanner comprises a focusing lens configured to focus the rays emitted by the radiation source onto the sample, and said focusing lens comprises an F/θ lens.

* * * * *